United States Patent
Osborne

(10) Patent No.: US 7,763,045 B2
(45) Date of Patent: Jul. 27, 2010

(54) REMOVABLE VENA CAVA FILTER

(75) Inventor: Thomas A. Osborne, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 1091 days.

(21) Appl. No.: 10/776,721

(22) Filed: Feb. 11, 2004

(65) Prior Publication Data

US 2004/0230220 A1  Nov. 18, 2004

Related U.S. Application Data

(60) Provisional application No. 60/446,711, filed on Feb. 11, 2003.

(51) Int. Cl.
*A61F 2/01* (2006.01)

(52) U.S. Cl. .................................................. 606/200

(58) Field of Classification Search ............... 606/200; 623/1.15
See application file for complete search history.

(56) References Cited

U.S. PATENT DOCUMENTS

| | | |
|---|---|---|
| 2,281,448 A | 4/1942 | Mathey |
| 3,174,851 A | 3/1965 | Buehler |
| 3,334,629 A | 8/1967 | Cohn |
| 3,540,431 A | 11/1970 | Mobin-Uddin |
| 3,868,956 A | 3/1975 | Alfidi et al. |
| 3,952,747 A | 4/1976 | Kimmell, Jr. |
| 4,425,908 A | 1/1984 | Simon |
| 4,494,531 A | 1/1985 | Gianturco |
| 4,619,246 A | 10/1986 | Molgaard-Nielsen et al. |
| 4,643,184 A | 2/1987 | Mobin-Uddin |
| 4,655,771 A | 4/1987 | Wallsten |
| 4,665,906 A | 5/1987 | Jervis |
| 4,688,553 A | 8/1987 | Metals |
| 4,727,873 A | 3/1988 | Mobin-Uddin |
| 4,759,757 A | 7/1988 | Pinchuk |
| 4,781,177 A | 11/1988 | Lebigot |
| 4,793,348 A | 12/1988 | Palmaz |
| 4,817,600 A | 4/1989 | Herms et al. |
| 4,830,003 A | 5/1989 | Wolff et al. |
| 4,832,055 A | 5/1989 | Palestrant |
| 4,856,516 A | 8/1989 | Hillstead |
| 4,873,978 A | 10/1989 | Ginsburg |
| 4,943,297 A | 7/1990 | Saveliev et al. |
| 4,950,227 A | 8/1990 | Savin et al. |
| 4,954,126 A | 9/1990 | Wallsten |
| 4,957,501 A | 9/1990 | Lahille et al. |
| 4,969,891 A | 11/1990 | Gewertz |
| 4,990,156 A | 2/1991 | Lefebvre |
| 5,037,377 A | 8/1991 | Alonso |
| 5,059,205 A | 10/1991 | El-Nounou et al. |
| 5,061,275 A | 10/1991 | Wallsten et al. |

(Continued)

*Primary Examiner*—Anhtuan T Nguyen
*Assistant Examiner*—Ryan J Severson
(74) *Attorney, Agent, or Firm*—Brinks Hofer Gilson & Lione

(57) ABSTRACT

A removable filter for capturing thrombi in a blood vessel. The filter comprises a plurality of primary struts having first ends connected to each other to define a central axis of the filter. Each primary strut has a curved member extending from the central axis and terminates at an anchoring hook to engage the blood vessel at a first axial plane. The filter further comprises a plurality of secondary struts connected to the curved members of the primary struts and extending therefrom to a free end at a second axial plane to centralize the filter in the blood vessel.

18 Claims, 5 Drawing Sheets

U.S. PATENT DOCUMENTS

| | | | |
|---|---|---|---|
| 5,067,957 A | 11/1991 | Jervis | |
| 5,071,407 A | 12/1991 | Termin et al. | |
| 5,108,418 A * | 4/1992 | Lefebvre | 606/200 |
| 5,108,419 A | 4/1992 | Reger et al. | |
| 5,133,733 A | 7/1992 | Rasmussen et al. | |
| 5,135,516 A | 8/1992 | Sahatjian et al. | |
| 5,147,379 A | 9/1992 | Sabbaghian et al. | |
| 5,152,777 A | 10/1992 | Goldberg et al. | |
| 5,160,342 A | 11/1992 | Reger et al. | |
| 5,190,546 A | 3/1993 | Jervis | |
| 5,217,484 A | 6/1993 | Marks | |
| 5,221,261 A | 6/1993 | Termin et al. | |
| 5,224,953 A | 7/1993 | Morgentaler | |
| 5,234,458 A | 8/1993 | Metais | |
| 5,242,462 A | 9/1993 | El-Nounou et al. | |
| 5,300,086 A | 4/1994 | Gory et al. | |
| 5,304,121 A | 4/1994 | Sahatjian | |
| 5,304,200 A | 4/1994 | Spaulding | |
| 5,324,304 A * | 6/1994 | Rasmussen | 606/200 |
| 5,329,942 A | 7/1994 | Gunther et al. | |
| 5,344,427 A | 9/1994 | Cottenceau et al. | |
| 5,350,398 A | 9/1994 | Pavcnik et al. | |
| 5,370,657 A | 12/1994 | Irie | |
| 5,375,612 A | 12/1994 | Cottenceau et al. | |
| 5,382,261 A | 1/1995 | Palmaz | |
| 5,383,887 A | 1/1995 | Nadal | |
| 5,405,377 A | 4/1995 | Cragg | |
| 5,413,586 A | 5/1995 | Dibie et al. | |
| 5,421,832 A | 6/1995 | Lefebvre | |
| 5,476,508 A | 12/1995 | Amstrup | |
| 5,522,822 A | 6/1996 | Phelps et al. | |
| 5,527,338 A | 6/1996 | Purdy | |
| 5,540,712 A | 7/1996 | Kleshinski et al. | |
| 5,549,626 A | 8/1996 | Miller et al. | |
| 5,549,629 A | 8/1996 | Thomas et al. | |
| 5,601,595 A | 2/1997 | Smith | |
| 5,626,605 A | 5/1997 | Irie et al. | |
| 5,630,801 A | 5/1997 | Roussigne et al. | |
| 5,634,942 A | 6/1997 | Chevillon et al. | |
| 5,649,953 A | 7/1997 | Lefebvre | |
| 5,669,933 A | 9/1997 | Simon et al. | |
| 5,681,347 A | 10/1997 | Cathcart et al. | |
| 5,683,411 A | 11/1997 | Kavteladze et al. | |
| 5,695,519 A | 12/1997 | Summers et al. | |
| 5,709,704 A | 1/1998 | Nott et al. | |
| 5,720,764 A | 2/1998 | Naderlinger | |
| 5,725,550 A | 3/1998 | Nadal | |
| 5,746,767 A | 5/1998 | Smith | |
| 5,755,778 A | 5/1998 | Kleshinski | |
| 5,755,790 A | 5/1998 | Chevillon et al. | |
| 5,776,162 A | 7/1998 | Kleshinski | |
| 5,800,457 A | 9/1998 | Gelbfish | |
| 5,800,525 A | 9/1998 | Bachinski et al. | |
| 5,807,398 A | 9/1998 | Shaknovich | |
| 5,810,874 A | 9/1998 | Lefebvre | |
| 5,836,968 A | 11/1998 | Simon et al. | |
| 5,836,969 A * | 11/1998 | Kim et al. | 606/200 |
| 5,843,244 A | 12/1998 | Pelton et al. | |
| 5,853,420 A | 12/1998 | Chevillon et al. | |
| 5,895,399 A | 4/1999 | Barbut et al. | |
| 5,902,317 A | 5/1999 | Kleshinski et al. | |
| 5,916,235 A | 6/1999 | Guglielmi | |
| 5,928,260 A | 7/1999 | Chin et al. | |
| 5,928,261 A | 7/1999 | Ruiz | |
| 5,938,683 A | 8/1999 | Lefebvre | |
| 5,951,585 A | 9/1999 | Cathcart et al. | |
| 5,976,172 A | 11/1999 | Homsma et al. | |
| 5,984,947 A | 11/1999 | Smith | |
| 6,007,557 A | 12/1999 | Ambrisco et al. | |
| 6,007,558 A | 12/1999 | Ravenscroft et al. | |
| 6,013,093 A | 1/2000 | Nott et al. | |
| 6,080,178 A | 6/2000 | Meglin | |
| 6,086,610 A | 7/2000 | Duerig et al. | |
| 6,126,673 A | 10/2000 | Kim et al. | |
| 6,129,755 A | 10/2000 | Mathis et al. | |
| 6,146,404 A | 11/2000 | Kim et al. | |
| 6,152,144 A | 11/2000 | Lesh et al. | |
| 6,156,055 A | 12/2000 | Ravenscroft | |
| 6,156,061 A | 12/2000 | Wallace et al. | |
| 6,179,851 B1 | 1/2001 | Barbut et al. | |
| 6,179,859 B1 | 1/2001 | Bates et al. | |
| 6,179,861 B1 | 1/2001 | Khosravi et al. | |
| 6,193,739 B1 | 2/2001 | Chevillon et al. | |
| 6,231,589 B1 | 5/2001 | Wessman et al. | |
| 6,241,738 B1 | 6/2001 | Dereume | |
| 6,241,746 B1 | 6/2001 | Bosma et al. | |
| 6,245,012 B1 | 6/2001 | Kleshinski | |
| 6,245,088 B1 | 6/2001 | Lowery | |
| 6,251,122 B1 | 6/2001 | Tsukernik | |
| 6,258,026 B1 | 7/2001 | Ravenscroft et al. | |
| 6,267,776 B1 | 7/2001 | O'Connell | |
| 6,273,900 B1 | 8/2001 | Nott et al. | |
| 6,273,901 B1 | 8/2001 | Whitcher et al. | |
| 6,277,139 B1 | 8/2001 | Levinson et al. | |
| 6,287,315 B1 | 9/2001 | Wijeratne et al. | |
| 6,287,329 B1 | 9/2001 | Duerig et al. | |
| 6,306,163 B1 | 10/2001 | Fitz | |
| 6,312,454 B1 | 11/2001 | Stockel et al. | |
| 6,312,455 B2 | 11/2001 | Duerig et al. | |
| 6,325,815 B1 | 12/2001 | Kusleika et al. | |
| 6,331,183 B1 | 12/2001 | Suon | |
| 6,342,062 B1 | 1/2002 | Suon et al. | |
| 6,342,063 B1 | 1/2002 | DeVries et al. | |
| 6,342,067 B1 | 1/2002 | Mathis et al. | |
| 6,346,116 B1 | 2/2002 | Brooks et al. | |
| 6,364,895 B1 | 4/2002 | Greenhalgh | |
| 6,391,045 B1 | 5/2002 | Kim et al. | |
| 6,436,120 B1 | 8/2002 | Meglin | |
| 6,436,121 B1 | 8/2002 | Blom | |
| 6,447,530 B1 | 9/2002 | Ostrovsky et al. | |
| 6,468,290 B1 | 10/2002 | Weldon et al. | |
| 6,482,222 B1 | 11/2002 | Bruckheimer et al. | |
| 6,485,502 B2 | 11/2002 | DonMichael et al. | |
| 6,506,205 B2 | 1/2003 | Goldberg et al. | |
| 6,511,503 B1 | 1/2003 | Burkett et al. | |
| 6,517,559 B1 | 2/2003 | O'Connell | |
| 6,527,962 B1 | 3/2003 | Nadal | |
| 6,540,767 B1 | 4/2003 | Walak et al. | |
| 6,551,342 B1 | 4/2003 | Shen et al. | |
| 6,558,404 B2 | 5/2003 | Tsukernik | |
| 6,569,183 B1 | 5/2003 | Kim et al. | |
| 6,579,303 B2 | 6/2003 | Amplatz | |
| 6,589,266 B2 | 7/2003 | Whitcher et al. | |
| 6,602,226 B1 | 8/2003 | Smith et al. | |
| 7,147,649 B2 * | 12/2006 | Thomas | 606/200 |
| 2001/0000799 A1 | 5/2001 | Wessman et al. | |
| 2001/0011181 A1 | 8/2001 | DiMatteo | |
| 2001/0023358 A1 | 9/2001 | Tsukernik | |
| 2001/0034547 A1 | 10/2001 | Hall et al. | |
| 2001/0034548 A1 | 10/2001 | Vrba et al. | |
| 2001/0037126 A1 | 11/2001 | Stack et al. | |
| 2001/0039432 A1 | 11/2001 | Whitcher et al. | |
| 2002/0016624 A1 | 2/2002 | Patterson et al. | |
| 2002/0032460 A1 | 3/2002 | Kusleika et al. | |
| 2002/0039445 A1 | 4/2002 | Abe et al. | |
| 2002/0055767 A1 | 5/2002 | Forde et al. | |
| 2002/0087187 A1 | 7/2002 | Mazzocchi et al. | |
| 2002/0099431 A1 | 7/2002 | Armstrong et al. | |
| 2002/0116024 A1 | 8/2002 | Goldberg et al. | |
| 2002/0133217 A1 | 9/2002 | Sirhan et al. | |
| 2002/0138097 A1 | 9/2002 | Ostrovsky et al. | |
| 2002/0156520 A1 | 10/2002 | Boylan et al. | |
| 2002/0161393 A1 | 10/2002 | Demond et al. | |
| 2002/0169474 A1 | 11/2002 | Kusleika et al. | |

| | | | | | |
|---|---|---|---|---|---|
| 2002/0169495 A1 | 11/2002 | Gifford et al. | 2003/0097145 A1 | 5/2003 | Goldberg et al. |
| 2002/0183782 A1 | 12/2002 | Tsugita et al. | 2003/0109897 A1 | 6/2003 | Walak et al. |
| 2002/0193827 A1 | 12/2002 | McGuckin, Jr. et al. | 2003/0125790 A1 | 7/2003 | Fastovsky et al. |
| 2002/0193874 A1 | 12/2002 | Crowley | 2003/0125793 A1 | 7/2003 | Vesely |
| 2003/0018343 A1 | 1/2003 | Mathis | 2003/0130681 A1 | 7/2003 | Ungs |
| 2003/0028238 A1 | 2/2003 | Burkett et al. | 2003/0144686 A1 | 7/2003 | Martinez et al. |
| 2003/0040772 A1 | 2/2003 | Hyodoh et al. | 2003/0153943 A1 | 8/2003 | Michael et al. |
| 2003/0055481 A1 | 3/2003 | McMorrow | | | |

\* cited by examiner

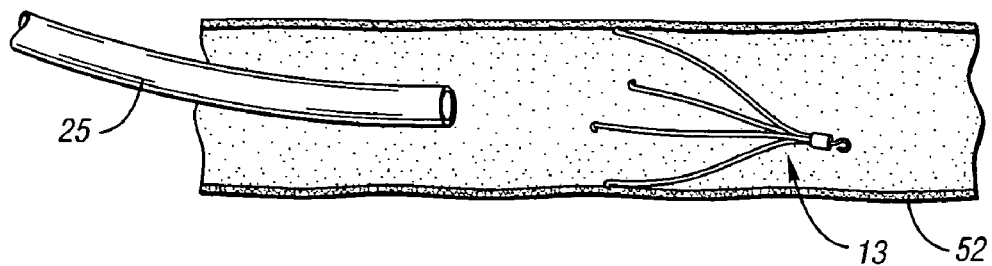
*Fig. 1 (PRIOR ART)*
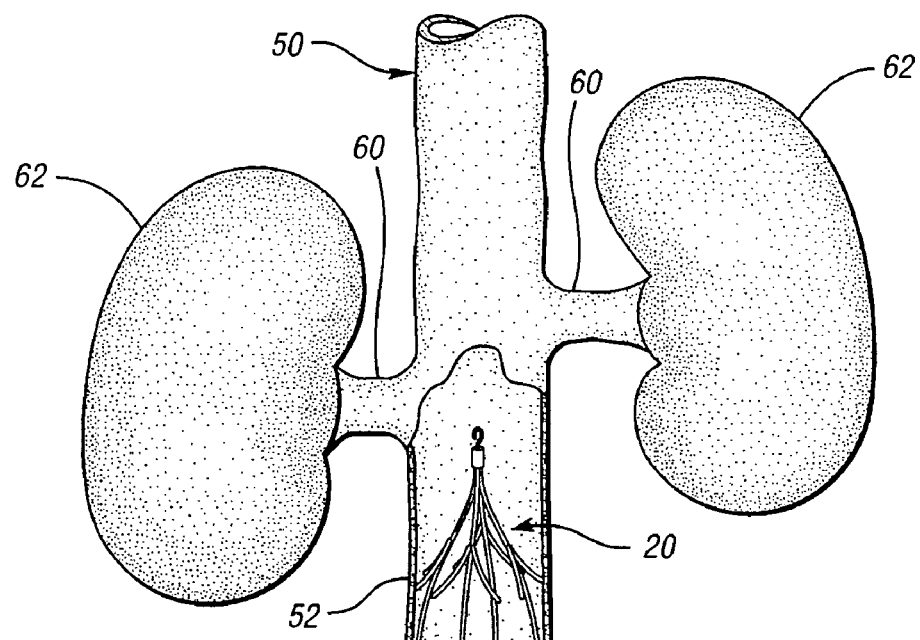
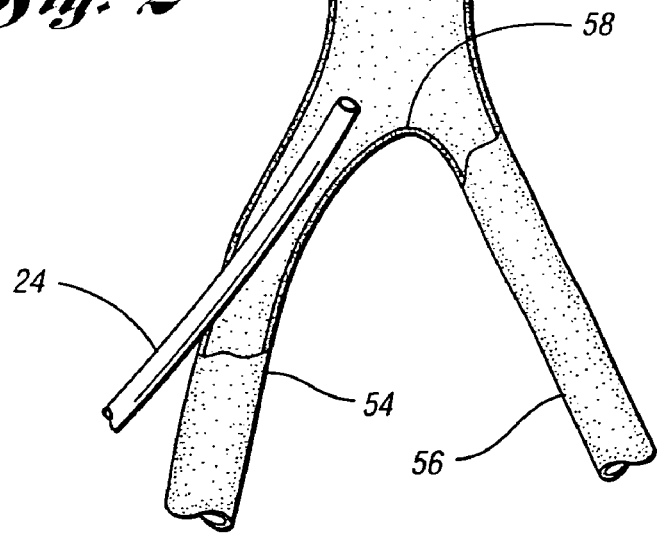
*Fig. 2*

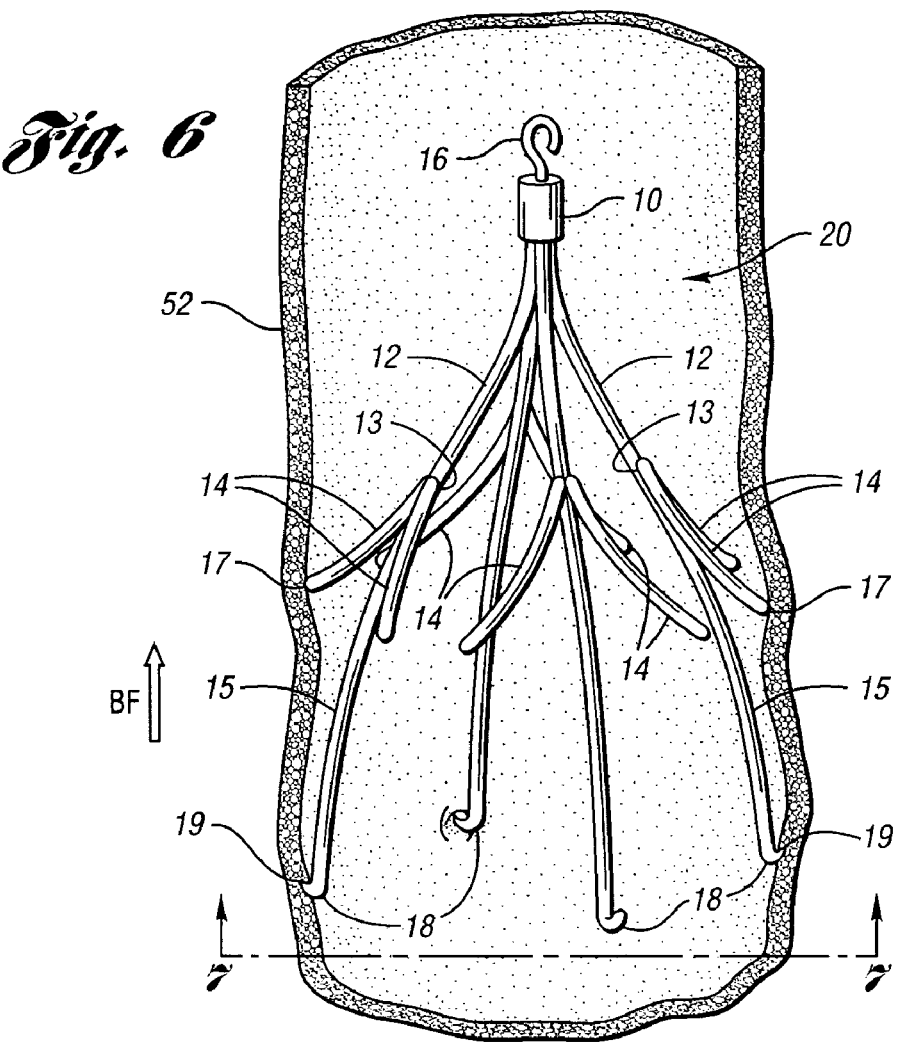
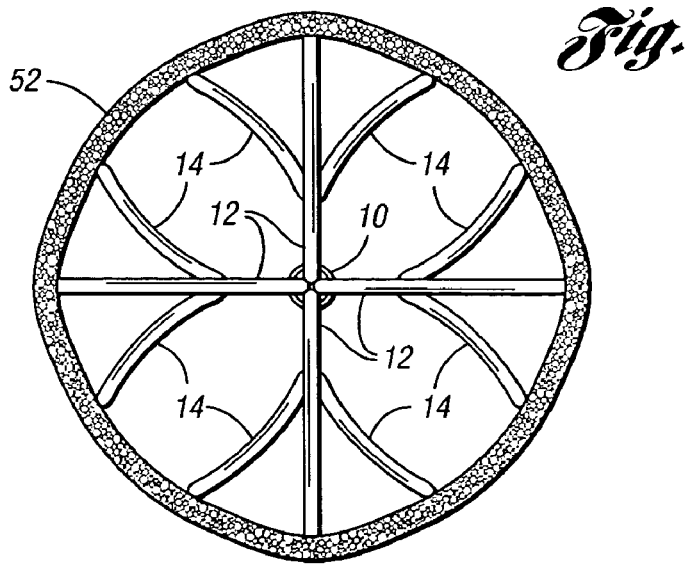

United States Patent

US 7,763,045 B2

REMOVABLE VENA CAVA FILTER

CROSS-REFERENCE TO RELATED APPLICATIONS

This application claims priority to U.S. Provisional Application No. 60/446,711, filed Feb. 11, 2003, entitled "Removable Vena Cava Clot Filter."

BACKGROUND OF THE INVENTION

The present invention relates to medical devices. More particularly, the invention relates to a removable vena cava clot filter that can be percutaneously placed in and removed from the vena cava of a patient.

Filtering devices that are percutaneously placed in the vena cava have been available for over thirty years. A need for filtering devices arises in trauma patients, orthopedic surgery patients, neurosurgery patients, or in patients having medical conditions requiring bed rest or non-movement. During such medical conditions, the need for filtering devices arises due to the likelihood of thrombosis in the peripheral vasculature of patients wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

A filtering device can be deployed in the vena cava of a patient when, for example, anticoagulant therapy is contraindicated or has failed. Typically, filtering devices are permanent implants, each of which remains implanted in the patient for life, even though the condition or medical problem that required the device has passed. In more recent years, filters have been used or considered in preoperative patients and in patients predisposed to thrombosis which places the patient at risk for pulmonary embolism.

The benefits of a vena cava filter have been well established, but improvements may be made. For example, filters generally have not been considered removable from a patient due to the likelihood of endotheliosis of the filter during treatment. After deployment of a filter in a patient, proliferating intimal cells begin to accumulate around the filter struts which contact the wall of the vessel. After a length of time, such ingrowth prevents removal of the filter without risk of trauma, requiring the filter to remain in the patient. As a result, there has been a need for an effective filter that can be removed after the underlying medical condition has passed.

Moreover, conventional filters commonly become off-centered or tilted with respect to the hub of the filter and the longitudinal axis of the vessel in which it has been inserted. As a result, the filter including the hub and the retrieval hook engage the vessel wall along their lengths and potentially become endothelialized therein. This condition is illustrated in prior art FIG. 1 in which a prior art filter 13 has been delivered through a delivery sheath 25 into a blood vessel 51. In the event of this occurrence, there is a greater likelihood of endotheliosis of the filter to the blood vessel along a substantial length of the filter wire. As a result, the filter becomes a permanent implant in a shorter time period than otherwise.

Some filters have been designed so that the filter has minimal contact with the vessel wall. Ideally, some filters can be removed after several weeks with minimal difficulty and little injury to the vessel wall. One such filter is described in U.S. Pat. No. 5,836,968. The filter is designed so that the filter wires or struts are not positioned parallel to the vessel walls or not in contact with the vessel walls for a substantial portion of the length of the filters. The ends of the struts contact the vessel walls and provide anchoring to reduce the likelihood of filter migration. When the filter is removed, a wire is docked to one end of the device while a sheath or sleeve is passed over the wire. Using counter traction by pulling the wire while pushing the sheath, the sheath is passed over the filter and the filter struts are retracted from the vessel wall. In this way, only small point lesions are created where the filter was attached to the vessel wall.

The filter of U.S. Pat. No. 5,836,968 teaches two levels of oppositely expanding filter wires or struts to insure that the filter is properly aligned in the lumen of the vessel. If the filter tilts or becomes misaligned with the central axis of the vessel, the filter wires will contact the wall of the vessel along a greater area, and become endothelialized. As a result of the two levels, removal of the filter from the blood vessel becomes impossible or at least difficult.

Additionally, the configuration of the second level of filter wires in the device of U.S. Pat. No. 5,836,968 provides a filter which may be too long for the segment of the vessel that the filter would normally be placed. The normal placement segment of a vena cava filter is between the femoral veins and the renal veins. If the lower part of the filter extends into the femoral veins, filtering effectiveness will be compromised. Moreover, it is not desirable to have filter wires crossing the origin of the renal veins, since the filter wires may interfere with the flow of blood from the kidneys. In the device disclosed in U.S. Pat. No. 5,836,968, both levels of filter wires are attached at one point as a bundle at the central axis of the filter. The resulting diameter of this bundle of filter wires results in a filter that may be too large for easy placement and becomes an obstacle to blood flow in the vena cava.

BRIEF SUMMARY OF THE INVENTION

The present invention provides a vena cava filter comprising struts configured to align the filter about the center axis of a blood vessel and minimize engagement with the blood vessel. The filter comprises a plurality of primary struts, each of which having a first end. A hub axially connects the first ends of the struts to define a central axis of the filter. Each primary strut has a curved member extending from the central axis. Each curved member terminates at an anchoring hook to engage the blood vessel at a first axial plane and secure the filter in the blood vessel. Each anchoring hook includes a barb formed at an angle relative to the strut to allow a removal sheath to be advanced over the filter and allow the hooks to be removed straight away from the vessel wall, resulting in minimal vessel damage. The filter further comprises a plurality of secondary struts. Each secondary strut is connected to one of the curved members and extends therefrom to a free end for engaging the blood vessel at a second axial plane, aligning the filter in the blood vessel.

In one embodiment, a set of at least two secondary struts are connected to the curved member of one primary strut. The set of secondary struts extend radially from each side of the primary strut, forming a netting configuration of the filter. In another embodiment, one secondary strut is connected to the curved member of one primary strut. The secondary strut extends from the primary strut and is in radial alignment with the primary strut, avoiding interference with blood flow.

In a collapsed configuration, the vena cava filter occupies a reduced diameter, since the hub is the origin to only primary struts. In an expanded configuration, the hub occupies a reduced cross-sectional area. As a result, interference with blood flow is lessened in the vena cava.

In an expanded configuration, the vena cava filter occupies a reduced length, since the secondary struts merely extend within the axial length of the primary struts. As a result, the filter can more easily be placed in the vena cava of a patient, lessening the risk of interference in the femoral and renal veins.

Further aspects, features, and advantages of the invention will become apparent from consideration of the following description and the appended claims when taken in connection with the accompanying drawings.

BRIEF DESCRIPTION OF THE DRAWINGS

FIG. 1 is a side view of a prior art filter deployed in a blood vessel;

FIG. 2 is an illustration of the anatomy of the renal veins, the femoral veins, and the vena cava in which one embodiment of a vena cava filter of the present invention is deployed;

FIG. 6 is a cross-sectional view of a blood vessel in which the filter of FIG. 3 has been deployed;

FIG. 7 is a cross-sectional view of the blood vessel of FIG. 6 taken along line 7-7;

DETAILED DESCRIPTION OF THE INVENTION

Figure 3:
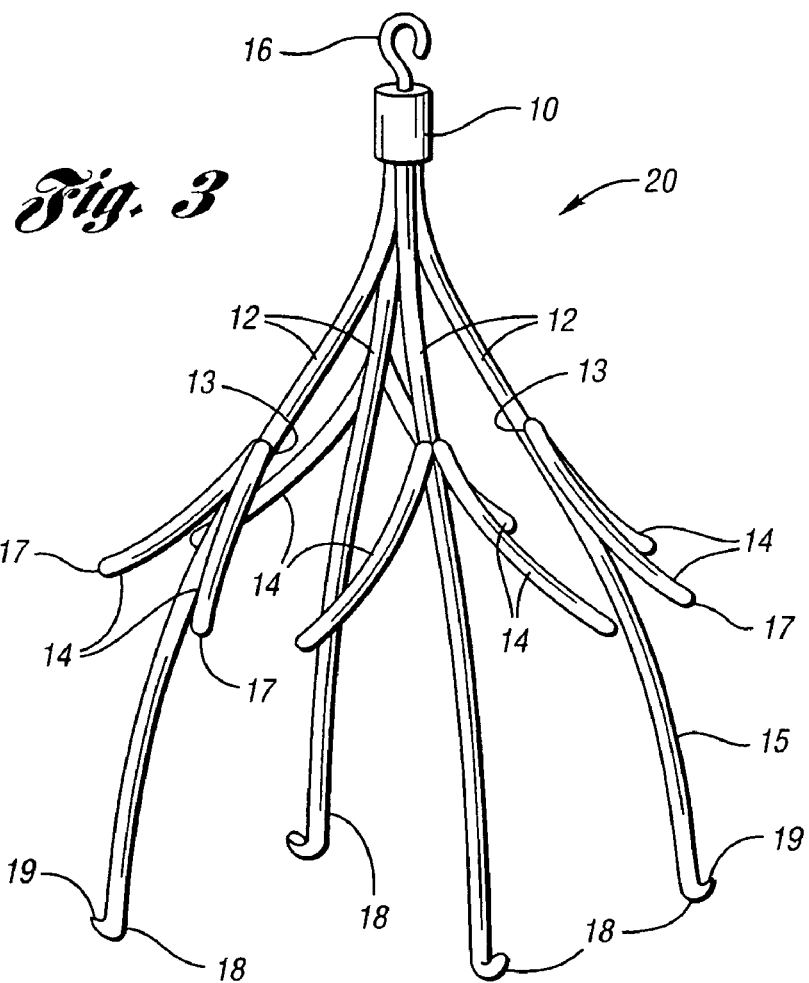
FIG. 3 is a side perspective view of one embodiment of the vena cava filter of the present invention.

In accordance with a first embodiment of the present invention, FIG. 2 illustrates a vena cava filter 20 implanted in the vena cava 50 for the purpose of lysing or capturing thrombi carried by the blood flowing through the femoral veins 54, 56 toward the heart and into the pulmonary arteries. As shown, the femoral veins from the legs merge at juncture 58 into the vena cava 50. The renal veins 60 from the kidneys 62 join the vena cava 50 downstream of juncture 58. The portion of the vena cava 50, between the juncture 58 and the renal veins 60, defines the inferior vena cava 52 in which the vena cava filter 20 has been percutaneously deployed through one of the femoral veins 54. Preferably, the vena cava filter 20 has a length smaller than the length of the inferior vena cava 52. If the lower part of the filter extends into the femoral veins, filtering effectiveness will be compromised and if the filter wires cross over the origin of the renal veins the filter wires might interfere with the flow of blood from the kidneys.

The first embodiment of the present invention will be discussed with reference to FIGS. 3-8 in which filter 20 is shown. FIG. 3 illustrates filter 20 comprising four primary struts 12 each having first ends that emanate from a hub 10. Hub 10 secures the first ends of primary struts 12 together in a compact bundle to define a central or longitudinal axis of the filter. The hub 10 has a minimal diameter for the size of wire used to form the struts. Preferably, the primary struts 12 are formed from stainless steel wire, MP35N, Nitinol, or any other suitable superelastic material that will result in a self-opening or self-expanding filter. In this embodiment, the primary struts 12 are formed from wire having a round cross-section with a diameter of about 0.015 inches. Of course, it is not necessary that the primary struts have a round cross-section. For example, the primary struts could have a square shaped or other suitable shaped cross section without falling beyond the scope or spirit of the present invention.

Each primary strut 12 is formed with a first curved portion 13 that is configured to bend away from the longitudinal or central axis of the filter 20 and a second curved portion 15 that is configured to bend toward the longitudinal axis of the filter 20. Each primary strut 12 maintains a non-parallel relationship with the longitudinal axis of the filter 20. The primary struts 12 terminate at anchoring hooks 18 that will anchor in the vessel wall when the filter 20 is deployed at a delivery location in the blood vessel. When the filter is deployed, the anchoring hooks define a first axial plane to secure the filter in the blood vessel. The anchoring hooks 18 prevent the filter 20 from migrating from the delivery location in the blood vessel where it has been deposited. The primary struts 12 are shaped and dimensioned such that, when the filter 20 is deployed and expanded, the filter 20 has a diameter of about 35 mm and a length of about 5 cm. For example, when expanded, the filter 20 may have a diameter of between about 30 mm and 40 mm, and a length of between about 3 cm and 7 cm. The primary struts 12 have sufficient spring strength that when the filter is deployed the anchoring hooks 18 will anchor into the vessel wall.

In this embodiment, each primary strut 12 has two secondary struts 14 secured thereto by laser welding, brazing, crimping or any suitable process that will avoid damaging the material or adding to the thickness of the filter and thus the size of the delivery system. The secondary struts 14 may be made from the same type of material as the primary struts. However, the secondary struts may have a smaller diameter, e.g., about 0.012 inches, than the primary struts. Each of the secondary struts 14 is formed of a single curve and is secured to one of the primary struts 12 on its first curved portion 13 such that the secondary strut 14 becomes a continuation or an extension of the first curved portion 13 of the primary strut 12. In this embodiment, two secondary struts 14 flare away from each side of one primary strut 12 to form a part of a netting configuration of the filter 20.

When opened, free ends 17 of the secondary struts 14 will expand radially outwardly to a diameter of about 35 mm to engage the vessel wall. For example, the secondary struts 14 may expand radially outwardly to a diameter of between about 30 mm and 40 mm. The free ends 17 define a second axial plane where the vessel wall is engaged. The secondary struts 14 function to stabilize the position of the filter 10 about the center of the blood vessel in which it is deployed. As a result, the filter 20 has two layers or planes of struts longitudinally engaging the vessel wall of the filter. The length of the filter is preferably defined by the length of a single set of primary struts. Furthermore, the diameter of the hub 10 is defined by the size of a bundle containing the primary struts 12. In this embodiment, the eight secondary struts, although maintaining the filter in a centered attitude relative to the vessel wall and formed as a part of the netting configuration of the filter, minimally add to the diameter of the hub or the overall length of the filter.

Figure 4:
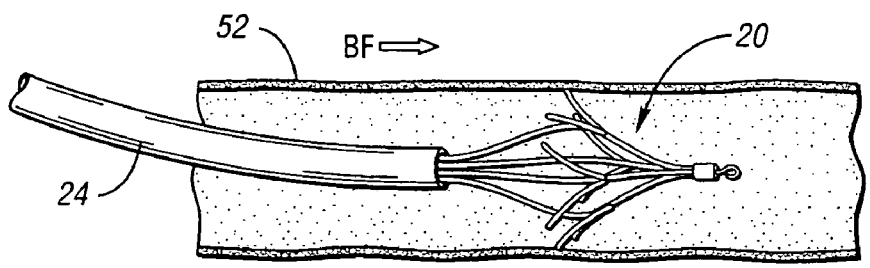
FIG. 4 is a cross-sectional view of a blood vessel showing the filter of the present invention partially deployed.

FIG. 4 illustrates the filter 20 partially deployed in inferior vena cava 52. For deployment of the filter 20, a delivery tube 24 is percutaneously inserted through the patient's vessels such that the distal end of the delivery tube is at the location of deployment. In this embodiment, a wire guide is preferably used to guide the delivery tube to the location of deployment. The filter is preferably inserted through the proximal end of the delivery tube 24 with the removal hook 16 leading and free ends of the primary struts 12 held by a filter retainer member. The filter retainer member may be connected to a pusher wire (not shown) that is fed through the proximal end of the delivery tube 24 until the filter reaches the distal end of the delivery tube 24. For a more complete disclosure of a filter delivery system that may be used to deliver the filter 20 to a desired location, reference may be made to U.S. Pat. No. 5,324,304 which is incorporated herein by reference.

As shown in FIG. 4, filter 20 is deployed leading with removal hook 16 from the delivery tube 24. The secondary struts expand first. When the free ends of the secondary struts emerge from the distal end of delivery tube 24, the secondary struts expand to an expanded position shown in FIG. 4. The free ends engage the inner wall of the vessel in which the filter is being deployed. The free ends of the secondary struts function to stabilize the attitude of filter 20 about the center of the blood vessel. The filter is then pushed further by the pusher wire (not shown) until it is fully deployed as shown in FIG. 5.

Figure 5:
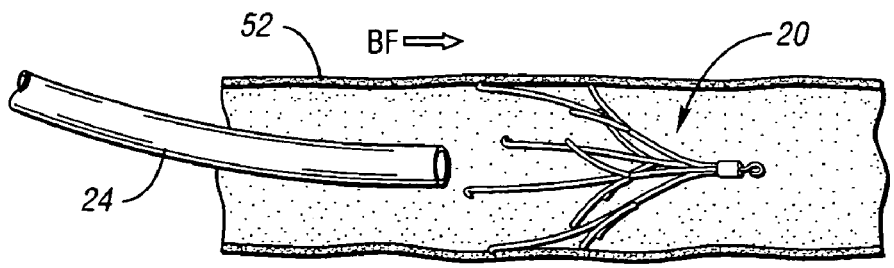
FIG. 5 is a cross-sectional view of a blood vessel showing the filter of the present invention fully deployed.

As shown in FIG. 5, the ends of the primary struts 12 and the secondary struts 14 are in engagement with the vessel wall. The anchoring hooks of the primary struts have anchored the filter at the location of deployment in the vessel, preventing the filter 20 from moving with the blood flow through the vessel. As a result, the filter 20 is supported by two sets of struts that are spaced axially along the length of the filter. The struts avoid engaging the vessel wall along their lengths and thus avoid becoming endothelialized in the vessel wall.

FIGS. 6 and 7 show the filter 20 fully expanded after being deployed in inferior vena cava 52. In FIG. 6, the inferior vena cava 52 has been broken away so that the filter 20 can be seen. The direction of the blood flow BF is indicated in FIG. 6 by the arrow that is labeled BF. The anchoring hooks 18 at the ends of the primary struts 12 are shown as being anchored in the inner lining of the inferior vena cava 52. The anchoring hooks 18 include barbs 19 that, in one embodiment, project toward the hub 10 of the filter. The barbs 19 function to retain the filter 20 in the location of deployment.

In this embodiment, the filter 20 is pushed in a direction BF of the blood flow by the pusher wire (not shown) during deployment. The pusher wire pushes the filter 20 from the delivery tube, causing the barbs 19 to move in the direction BF of the blood flow and secure anchoring hooks 18 in the inferior vena cava 52. The spring biased configuration of the primary struts 12 causes the anchoring hooks 18 to puncture the vessel wall and anchor the filter at the location of deployment. After initial deployment, the pressure of the blood flow on the filter 20 contributes in maintaining the barbs 19 anchored in the inner lining of the inferior vena cava 52. As seen in FIG. 6, the free ends 17 of secondary struts 14 also have a spring biased configuration to engage with the vessel wall. In this embodiment, the free ends 17 of secondary struts 14 are not provided with anchoring hooks, minimizing the trauma of retrieving the filter 20.

FIG. 7 illustrates a netting configuration formed by the primary struts 12, secondary struts 14, and the hub 10. The netting configuration shown in FIG. 7 functions to catch thrombi carried in the blood stream prior to reaching the heart and lungs to prevent the possibility of a pulmonary embolism. The netting configuration is sized to catch and stop thrombi that are of a size that are undesirable to be carried in the vasculature of the patient. As shown, the hub 10 houses a bundle of first ends of the four primary struts 14. Due to its compacted size, the hub minimally resists blood flow.

As seen in FIG. 6, the hub 10 and removal hook 16 are positioned downstream from the location at which the anchoring hooks 18 are anchored in the vessel. When captured by the struts, thrombi remains lodged in the filter. The filter along with the thrombi may then be percutaneously removed from the vena cava. When the filter 20 is to be removed, the removal hook 16 is preferably grasped by a retrieval instrument that is percutaneously introduced in the vena cava in the direction opposite to the direction in which the filter was deployed.

Figure 8:
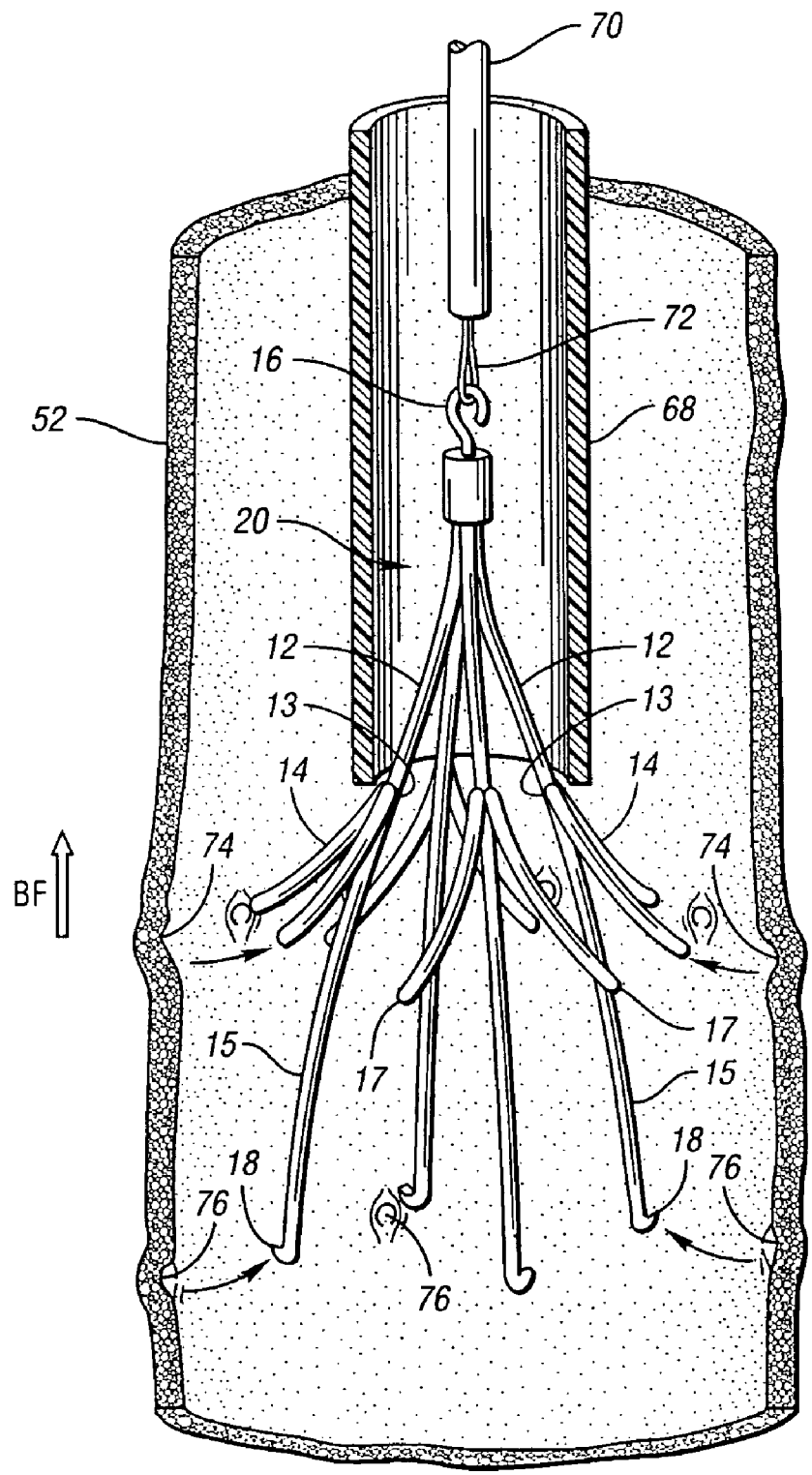
FIG. 8 is a cross-sectional view of a blood vessel showing a portion of a retrieval device for the filter in FIG. 3.

FIG. 8 illustrates part of a retrieval device 65 being used in a procedure for removing the filter 20 from the inferior vena cava 52. The retrieval device 65 is percutaneously introduced into the superior vena cava via the jugular vein. In this procedure, a removal catheter or sheath 68 of the retrieval device 65 is inserted into the superior vena cava. A wire 70 having a loop snare 72 at its distal end is threaded through the removal sheath 68 and is exited through the distal end of the sheath 68. The wire is then manipulated by any suitable means from the proximal end of the retrieval device such that the loop snare 72 captures the removal hook 16 of the filter 20. Using counter traction by pulling the wire 70 while pushing the sheath 68, the sheath 68 is passed over the filter. As the sheath 68 passes over the filter 20, the secondary struts 14 and then the primary struts 12 engage the edge of the sheath 68 and are caused to pivot at the hub 10 toward the longitudinal axis of the filter. The pivoting toward the longitudinal axis causes the ends of the struts 14 and 12 to be retracted from the vessel wall. In this way, only surface lesions 74 and small point lesions 76 on the vessel wall are created in the removal procedure. As shown, the surface lesions 74 are created by the ends of the secondary struts 14 and the small point legions 76 are created by the anchoring hooks 18 of the primary struts 12. However, it is to be noted that any other suitable procedure may be implemented to remove the filter from the patient.

Figure 9:
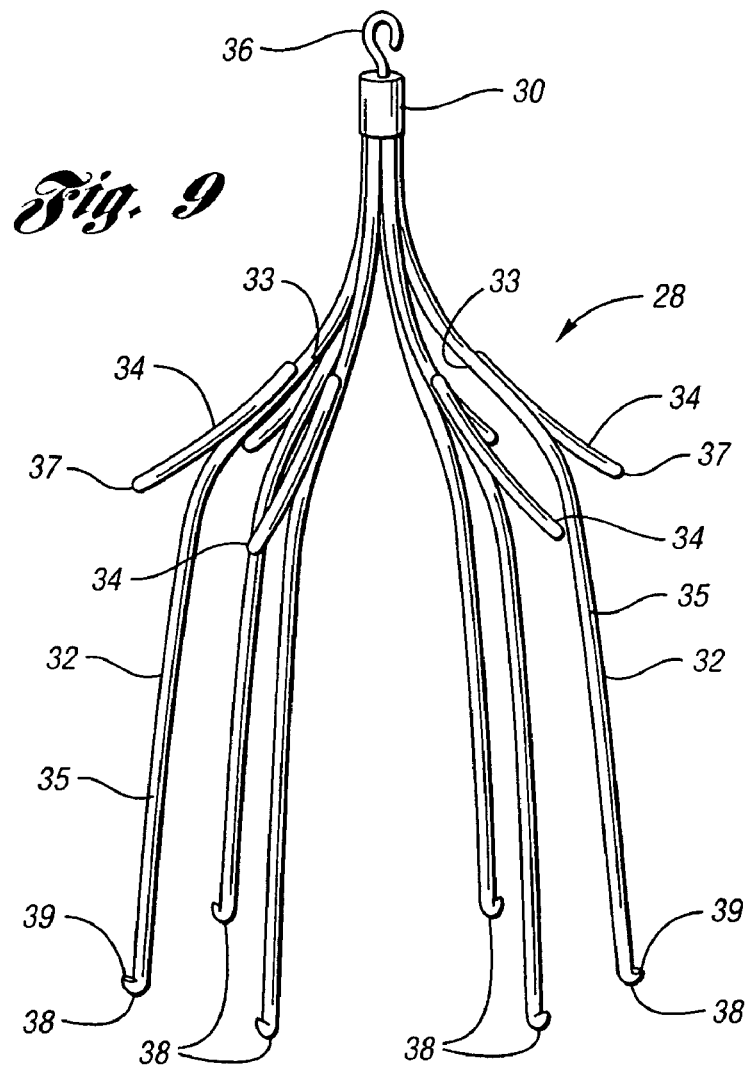
FIG. 9 is a side perspective view of a vena cava filter in accordance with another embodiment of the present invention.

A second embodiment of the present invention will be discussed with reference to FIGS. 9 and 10 in which a filter 28 is shown. FIG. 9 illustrates filter 28 comprising six primary struts 32 each having first ends that emanate from a hub 30. Hub 30 secures the first ends of primary struts 32 together in a compact bundle to define a central axis of the filter. Similar to the hub 10 in the first embodiment discussed above, the hub 30 in this embodiment has a minimal diameter for the size of wire used to form the struts.

The primary struts 32 in this embodiment are similar in structure to the primary struts 12 in the first embodiment above. For example, in the second embodiment, each primary strut 32 of the filter 28 includes first and second curved portions 33 and 35, removal hook 36, free ends 37, an anchoring hook 38, and a barb 39 which are respectively similar to the first and second curved portions 13 and 15, removal hook 16, free ends 17, the anchoring hook 18, and the barb 19 of the filter 28 in the first embodiment. Preferably, the primary struts 32 are shaped and dimensioned such that, when the filter 28 is deployed and expanded, the filter 28 has a diameter of about 35 mm and a length of about 5 cm. For example, when expanded, the filter 28 may have a diameter of between about 30 mm and 40 mm, and a length of between about 3 cm and 7 cm. The primary struts 32 have sufficient spring strength such that when the filter is deployed the anchoring hooks 38 will anchor into the vessel wall.

Preferably, the primary struts 32 are formed of the same material as the primary struts 12 mentioned above, e.g., stainless steel wire, MP35N, Nitinol, or any other suitable material. In this embodiment, the primary struts 32 are formed from wire having a round cross-section with a diameter of about 0.015 inches. As stated above, it is not necessary that the primary struts have a round cross-section.

In this embodiment, each primary strut 32 has one secondary strut 34 secured thereto by laser welding, brazing, crimping or any suitable process that will not damage the material or add to the thickness of the filter and thus the size of the delivery system. The secondary struts 34 may be made from the same type of material as the primary struts. Preferably, the secondary struts may have a smaller diameter, e.g., about 0.012 inches, than the primary struts. As in the first embodiment, each of the secondary struts 34 in this embodiment is formed of a single curve and is secured to one of the primary struts 32 on the first curved portion such that the secondary strut 34 becomes a continuation or extension of the first curved portion of the primary strut 32. As shown, each of the secondary struts 34 flares away from one primary strut 32 and is in radial alignment therewith.

When opened, the free ends of the secondary struts 34 will expand outwardly to a diameter of about 35 mm to engage the vessel wall. For example, the secondary struts 34 may expand outwardly to a diameter of between about 30 mm and 40 mm. Similar to the secondary struts 14 in the first embodiment, the secondary struts 34 in this embodiment function to stabilize the position of the filter 28 about the center of the blood vessel in which it is deployed. As a result, the filter 28 has two layers or planes of struts longitudinally engaging the vessel wall of the filter. The length of the filter is preferably defined by the length of a single set of primary struts. Furthermore, the diameter of the hub 30 is defined by the size of a bundle containing the primary struts 32. As in the first embodiment, the secondary struts in this embodiment, although maintaining the filter in a centered attitude relative to the vessel wall and formed as a part of a netting configuration of the filter, minimally add to the diameter of the hub or the overall length of the filter.

Figure 10:
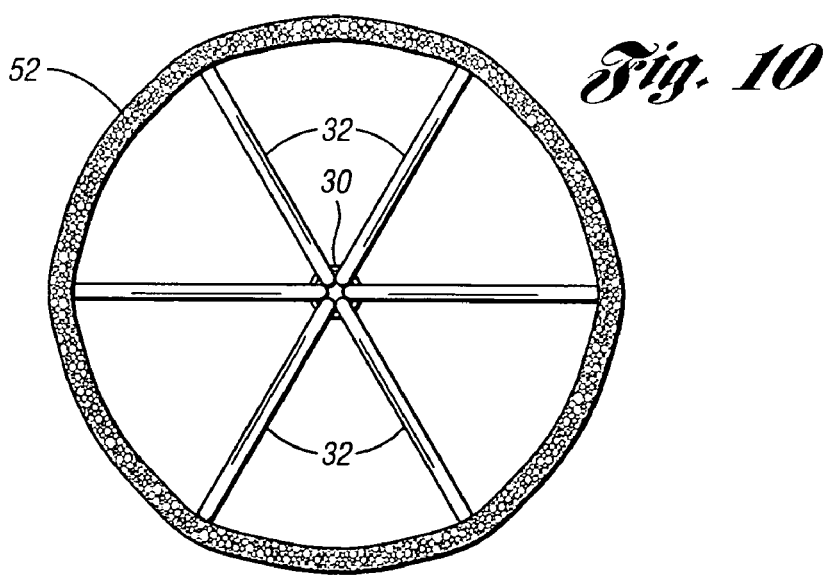
FIG. 10 is a cross-sectional view of a blood vessel in which the filter in FIG. 9 is disposed.

FIG. 10 illustrates the netting configuration of the filter 28 formed by the primary struts 32 and the hub 30. As shown, the secondary struts 34 are positioned behind and in alignment with the primary struts 32 and, thus, avoid substantially affecting blood flow. The netting configuration functions to catch thrombi carried in the blood stream prior to reaching the heart and lungs to prevent the possibility of a pulmonary embolism. The netting configuration is sized to catch and stop thrombi that are of a size that are undesirable to be carried in the vasculature of a patient. As shown, the hub 30 houses a bundle of ends of the six primary struts 34. Due to its compacted size, the hub minimally resists blood flow.

It is to be noted that the filter 28 may be deployed in the vena cava in the same manner previously discussed for filter 20 with reference to FIGS. 2, 4, and 5. Additionally, the filter 28 may be removed from the vena cava with the removal procedure previously discussed for filter 20 with reference to FIG. 8.

Although the embodiments of this device have been disclosed as being constructed from wire having a round cross section, it could also be cut from a tube of suitable material by laser cutting, electrical discharge machining or any other suitable process.

While the present invention has been described in terms of preferred embodiments, it will be understood, of course, that the invention is not limited thereto since modifications may be made to those skilled in the art, particularly in light of the foregoing teachings.

The invention claimed is:

1. A removable filter for capturing thrombi in a blood vessel, the filter comprising:
    a plurality of primary struts having first ends connected to each other to define a central axis of the filter, each primary strut having a curved member extending from the central axis and terminating at an anchoring hook to engage the blood vessel at a first axial plane, each curved member having a first curved portion configured to bend away from the central axis in a single curve along the length of each curved member and a second curved portion configured to bend toward the central axis along the length of each curved member; and
    a plurality of secondary struts connected to and contacting the curved members of the primary struts and extending therefrom to a free end at a second axial plane to centralize the filter in the blood vessel, the free end not contacting the plurality of primary struts, the primary struts and the secondary struts forming a minimal diameter defining a collapsed configuration of the filter and a maximum diameter defining an expanded configuration of the filter, each secondary strut being formed of a single curve and being secured to one of the first curved portions, wherein a set of at least two non-parallel secondary struts is connected to one primary strut, each secondary strut contacting no primary struts other than the one primary strut and each secondary strut contacting at least one other secondary strut in the expanded configuration.

2. The removable filter of claim 1 wherein the removable filter has a greater number of secondary struts than primary struts, the set of secondary struts extending radially from each side of the one primary strut.

3. The removable filter of claim 2, wherein the secondary struts of the set are not unitarily formed with one another.

4. The removable filter of claim 1 wherein the first and second curved portions are configured to have a non-parallel relationship with the central axis of the filter.

5. The removable filter of claim 1 wherein the anchoring hook includes a barb for engaging the wall of the blood vessel, the barb being configured to project toward the first end.

6. The removable filter of claim 1 further comprising:
    a hub configured to axially house the first ends of the plurality of primary struts; and
    a retrieval hook extending from the hub opposite the plurality of primary struts for removal of the filter from the blood vessel.

7. The removable filter of claim 1 wherein the second axial plane is defined between the first ends and the anchoring hooks of the plurality of primary struts.

8. The removable filter of claim 1 wherein each primary strut has a diameter of about 0.015 inch.

9. The removable filter of claim 1 wherein each primary strut is formed of a superelastic material.

10. The removable filter of claim 1 wherein each secondary strut has a diameter of 0.012 inch.

11. The removable filter of claim 1 wherein each secondary strut is formed of a superelastic material.

12. The removable filter of claim 1 wherein the primary struts and the secondary struts expand to a diameter of about 35 millimeters.

13. The removable filter of claim 12 wherein the length of each primary strut is about 5 centimeters.

14. The removable filter of claim 1 wherein the primary struts are configured to pivot at the first ends thereof to move between the collapsed and expanded configurations.

15. The removable filter of claim 1 wherein each secondary strut is connected to a primary strut by at least one of the following means: laser welding, brazing, or crimping.

16. The removable filter of claim 1 wherein each secondary strut is connected to a primary strut of the plurality of primary struts at a point about halfway between the central axis and an outer perimeter of the removable filter in the expanded configuration, the outer perimeter being defined by each anchoring hook.

17. The removable filter of claim 1 wherein the secondary strut forms a continuation of the single curve of the first curved portion of the primary strut in the expanded configuration, the secondary strut extending from and being in radial alignment with the primary strut.

18. A removable filter for capturing thrombi in a blood vessel, the filter comprising:
   a plurality of primary struts having first ends axially connected to each other to define a central axis of the filter, each primary strut having a curved member extending from the central axis and terminating at an anchoring hook to engage the blood vessel at a first axial plane, each curved member having a first curved portion configured to bend away from the central axis in a single curve along the length of each curved member and a second curved portion configured to bend toward the central axis along the length of each curved member; and
   a plurality of secondary struts connected to and contacting one of the curved members, each secondary strut extending therefrom to a free end at a second axial plane to centralize the filter in the blood vessel, the free end not contacting the plurality of primary struts, the primary struts and the secondary struts forming a minimal diameter defining a collapsed configuration of the filter and a maximum diameter defining an expanded configuration of the filter, the free ends of the secondary struts being configured to engage the blood vessel in the expanded configuration, each secondary strut being formed of a single curve and being secured to the first curved portion of the curved member such that the secondary strut forms a continuation of the single curve of the first curved portion in the expanded configuration, the secondary strut and the first curved portion having substantially the same radius of curvature in the expanded configuration,
   wherein a set of at least two secondary struts is connected to one primary strut, each secondary strut contacting no primary struts other than the one primary strut, and each secondary strut contacting at least one other secondary strut, the set of secondary struts extending radially from each side of the one primary strut, the removable filter having a greater number of secondary struts than primary struts, and
   wherein the secondary struts of the set are non-parallel.

* * * * *